United States Patent
Wittkampf

(10) Patent No.: US 10,080,602 B2
(45) Date of Patent: Sep. 25, 2018

(54) GENERATOR, COMBINATION OF A GENERATOR AND A CATHETER, AND METHOD FOR PROVIDING AN ELECTRICAL PULSE

(75) Inventor: Frederik Henricus Matheus Wittkampf, Lage Vuursche (NL)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 205 days.

(21) Appl. No.: 13/813,123

(22) PCT Filed: Jul. 30, 2010

(86) PCT No.: PCT/EP2010/061116
§ 371 (c)(1),
(2), (4) Date: Jan. 29, 2013

(87) PCT Pub. No.: WO2012/013243
PCT Pub. Date: Feb. 2, 2012

(65) Prior Publication Data
US 2013/0131662 A1 May 23, 2013

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1492* (2013.01); *A61B 2017/00212* (2013.01);
(Continued)

(58) Field of Classification Search
CPC ...... A61B 18/1206; A61B 2018/00702; A61B 2018/00708; A61B 2018/00761;
(Continued)

(56) References Cited

U.S. PATENT DOCUMENTS 5,706,823 A * 1/1998 Wodlinger ............... 600/509
6,212,426 B1 * 4/2001 Swanson ................. 600/510
(Continued)

OTHER PUBLICATIONS

PCT Application No. PCT/EP2010/061116, International Search Report and Written Opinion of the International Searching Authority dated Feb. 14, 2013.
(Continued)

*Primary Examiner* — Ronald Hupczey, Jr.
(74) *Attorney, Agent, or Firm* — Dykema Gossett PLLC

(57) ABSTRACT

The invention provides systems, methods, and apparatus for use in ablation procedures. The invention includes a generator with at least one indifferent lead and at least one catheter lead for connecting an indifferent electrode and a catheter provided with at least one electrode, a charging unit arranged to charge an amount of electrical energy and to discharge an electrical pulse of a predetermined magnitude between the two electrode leads, a power supply arranged to supply electrical energy to the charging unit, an input unit arranged for inputting an indication of the magnitude of the pulse, and a measuring unit arranged between the electrode leads for measuring at least one electrical property between the leads. Numerous additional aspects are provided.

18 Claims, 3 Drawing Sheets

(51) Int. Cl.
*A61B 17/00* (2006.01)
*A61B 18/00* (2006.01)

(52) U.S. Cl.
CPC ............... *A61B 2018/00351* (2013.01); *A61B 2018/00577* (2013.01); *A61B 2018/00702* (2013.01); *A61B 2018/00839* (2013.01); *A61B 2018/00875* (2013.01)

(58) Field of Classification Search
CPC ........... A61B 2018/00767; A61B 2018/00875; A61B 2018/00898; A61B 2018/00351
USPC .......................................................... 606/34
See application file for complete search history.

(56) References Cited

U.S. PATENT DOCUMENTS

| | | | | |
|---|---|---|---|---|
| 6,287,297 | B1 * | 9/2001 | Woodruff et al. ................ | 606/7 |
| 6,398,779 | B1 * | 6/2002 | Buysse .............. | A61B 18/1445 606/34 |
| 7,717,910 | B2 * | 5/2010 | Goble ................ | A61B 18/1206 606/34 |
| 7,862,565 | B2 * | 1/2011 | Eder et al. ....................... | 606/50 |
| 8,663,214 | B2 * | 3/2014 | Weinberg ........... | A61B 18/1206 606/34 |
| 2003/0055422 | A1 * | 3/2003 | Lesh .............................. | 606/41 |
| 2005/0203503 | A1 | 9/2005 | Edwards et al. | |
| 2007/0270795 | A1 * | 11/2007 | Francischelli ..... | A61B 18/1206 606/41 |

OTHER PUBLICATIONS

PCT Application No. PCT/EP2010/061116, International Preliminary Report on Patentability and Written Opinion of the International Searching Authority dated Feb. 2, 2012.

* cited by examiner

GENERATOR, COMBINATION OF A GENERATOR AND A CATHETER, AND METHOD FOR PROVIDING AN ELECTRICAL PULSE

CROSS-REFERENCE TO RELATED APPLICATIONS

This national stage patent application under 35 U.S.C. § 371 claims priority to PCT application no. PCT/EP2010/061116 filed Jul. 30, 2010, the disclosure of which is incorporated herein by reference for all purposes.

BACKGROUND

The present invention relates to a generator for use in an ablation procedure. The invention further relates to the combination of a catheter and a generator. The invention furthermore relates to a method for providing an electrical pulse between two electrode leads.

Generators for use in ablation procedures using a catheter are known and typically comprise a high-power, high frequency generator for generating a radio frequency (RF) pulse between two electrodes for damaging tissue, for instance cardiac tissue. In addition, heating by RF energy may cause blood clots.

Using this known combination of a generator and a catheter, cardiac tissue areas can be isolated, for instance to prevent fibrillation from originating from these areas. In particular the pulmonary vein antrum is a notorious source for atrial arrhythmias and atrial fibrillation.

Although RF-ablation is nowadays the preferred method for isolating cardiac tissue, the RF-ablation has the drawback that it is time consuming.

It is therefore an object of the present invention to provide a more efficient generator wherein the above mentioned drawbacks are at least partially improved.

SUMMARY

To meet that object, a generator according to appended claim 1 is provided.

In particular, according to the invention, there is provided a generator for use in an ablation procedure, comprising:
- at least one indifferent lead and at least one catheter lead for connecting an indifferent electrode and a catheter provided with at least one electrode;
- a charging unit arranged to charge an amount of electrical energy and to discharge an electrical pulse of a predetermined magnitude between the two electrode leads;
- a power supply arranged to supply electrical energy to the charging unit;
- an input unit arranged for inputting the magnitude of the pulse, and;
- a measuring unit arranged between the electrode leads for measuring at least one electrical property between the leads.

BRIEF DESCRIPTION OF THE DRAWINGS

Embodiments of the present invention are illustrated in the following drawings which depict an example embodiment according to the invention. These drawings are not intended to limit the scope of the invention.

DETAILED DESCRIPTION

Figure 1:
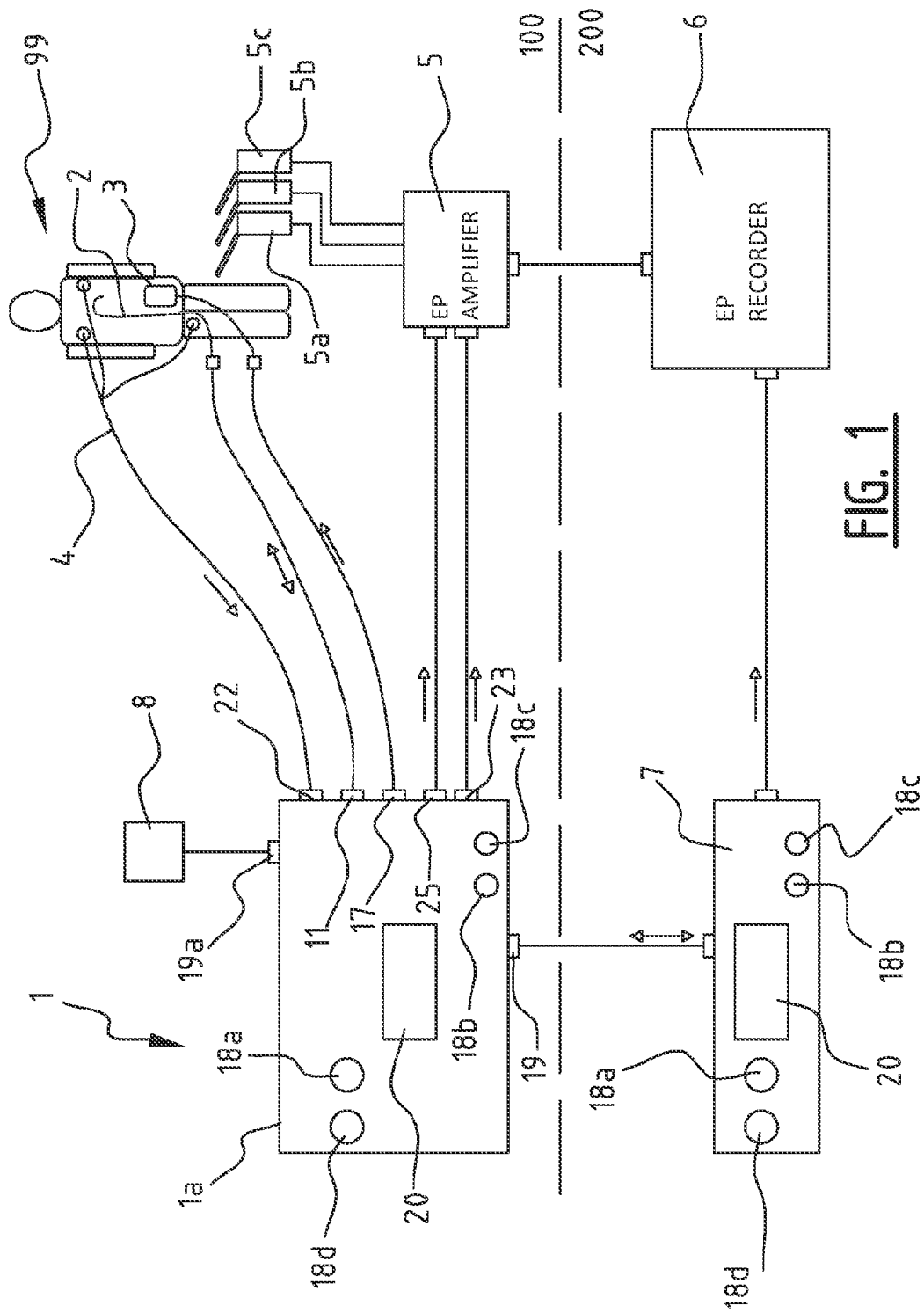
FIG. 1 schematically shows an example of a system for use in a DC ablation procedure according to embodiments of the invention.

The generator according to the invention is arranged for use in direct current (DC) ablation procedures and is thereto arranged to connect to a catheter provided with at least one electrode, preferably using a suitable connector. The catheter lead is hereby operable connected to said connector. Preferably a second connector, operable connected to the indifferent lead, is provided for connecting an indifferent electrode, for instance in the form of a skin patch. The generator is arranged to provide an electrical pulse between the two electrodes, i.e. the electrode of the catheter and the indifferent electrode. It should be remarked that it is also possible to connect for instance a catheter via a catheter connection or extension cable to the generator according to the invention.

The charging unit is arranged to build op electrical energy for instant discharge on demand for producing a pulse and preferably comprises a capacitive-discharge unit. Such units are for instance known from defibrillators. In particular, the charging unit comprises a capacitor charged by a power supply, for instance over a resistor.

The amount of electrical energy charged by the charging unit is adjustable on input by the physician using the input unit. The amount of charged energy is preferably adjusted by adjusting the charging voltage over the capacitor. The charging voltage is preferably between 1 to 10 kV. Preferably, the generator is provided with a charge actuator ('charge button') to allow a physician to initiate the charging.

The generator is preferably provided with a discharge actuator ('fire button') allowing the physician to discharge the charging unit. Preferably, the capacitor is switched to the leads, wherein the capacitor is discharged, preferably over an inductor.

The charging unit is preferably arranged to discharge a mono phase electrical pulse, i.e. a pulse with a single polarity. Preferably, the charging unit is arranged to discharge a substantially critically damped pulse. More preferably, the generator is arranged such that the catheter electrode used as cathode, wherein the indifferent electrode is used as anode. The charging unit is preferably arranged to discharge a pulse with a length between 2 and 10 ms, preferably approximately 6 ms.

Preferably the generator according to the invention the charging unit is arranged to discharge a pulse with a magnitude between approximately 100 to 400 Joule over approximately 60 Ohm.

According to the invention, a measuring unit is provided between the leads to measure or monitor at least one electrical property between the leads. As the amount of electrical energy used in direct current ablation procedures is substantially higher than in conventional ablation procedures, it is important to monitor these electrical properties between the leads. The risk of explosions and sparking associated with DC ablation near the electrode is hereby reduced.

A preferred embodiment of the generator further comprises a control unit which is arranged to adjust the magnitude of the electrical pulse discharged by the charging unit on the basis of the electrical property measured by the measuring unit. This allows feedback control of the discharged pulse. For instance in case of a measured abnormality or sudden change in an electrical property, the control unit is arranged to adjust the magnitude of the pulse, for instance by adjusting the magnitude to zero, i.e. suppressing the pulse. As discussed above, since the amount electrical energy used in DC procedures is high, a too high or a too low impedance between the electrodes may lead to unwanted injury to the patient, for instance due to sparks initiating at the electrodes due to too high local electrical densities at the electrode of the catheter. Automatic feedback control for the discharged electrical energy is thus advantageously.

Preferably, the generator comprises a housing containing the different units of the generator. This leads to a compact composition, allowing the generator to be used in clinical settings.

Preferably the measuring unit is arranged to determine the impedance between the electrode leads. The magnitude of the current discharged to the patient using the two electrodes connected to the two leads, is inversely proportional to the impedance or electrical resistance of the patient. Measuring the impedance between the leads is a measure of the impedance between the electrodes and therefore of the patient. The amount of actual electrical current or charge provided to the patient can hereby be predicted and preferably the control unit is arranged to adjust the magnitude of the electrical current or charge discharged by the charging unit on the basis of the measured impedance. The amount of electrical energy charging in the charging unit is preferably adjusted by adjusting the charging voltage over the charging unit, in particular the capacitor.

According to a further preferred embodiment, the control unit is arranged to determine whether a measured impedance is within a predetermined range of normal impedances and to provide output in case an impedance outside the range is measured. Preferably the control unit is arranged to suppress charging of the charging unit in case such an impedance is measured. It is also possible to warn the physician using an output device, for instance an audio or display device. For instance, in case a low or high impedances is measured, electrode placement in and/or on the patient may wrong. Preferably, said range is approximately 20 to 150 Ohm, more preferably 40 to 100 Ohm.

Preferably the measuring unit is arranged to determine the impedance between the electrode leads prior to discharge of the pulse. The amount of electrical energy provided to the patient can thus be adjusted prior to providing the pulse.

More preferably the input unit is arranged to input an electrical charge as measure of the magnitude of the pulse and wherein the control unit is arranged to adjust the amount of charged energy in the charging unit on the basis of the measured impedance for discharging a pulse between the leads with the inputted electrical charge. Instead of inputting the magnitude of the pulse in terms of the charging voltage as is known in the art, the physician is allowed to input the magnitude of the pulse in terms of the electrical energy, more preferably electrical charge to be provided to the patient. When the physician inputs the magnitude of the pulse in terms of energy, then he may presume a nominal impedance or resistance of the patient. The control unit will then automatically adjust that energy on the basis of the measured impedance or resistance.

The magnitude of the pulse is preferably inputted in terms of Joules or amperage. More preferably, the input unit is arranged to allow input of a magnitude of the pulse of between 100 and 500 J. More preferably, the input unit is provided with corresponding indications for the pulse magnitude. It may also be possible to input the magnitude of the pulse in terms of magnitude of the current.

The control unit is arranged to adjust the amount of electrical energy to be charged in the charging unit, preferably by adjusting the charging voltage, on the basis of the inputted electrical charge and the measured impedance.

According to a further preferred embodiment the measuring unit is arranged to measure an electrical property of the pulse, preferably the difference in voltage between the leads, over at least a time period of the pulse. By measuring the shape of the pulse, preferably the shape of the whole pulse, the occurrence of sparks at the electrode can be detected. In case of sparking at the electrode, the pulse shape is disturbed. A preferred pulse shape corresponds to half a period of sinus wave, whereas in case of sparking, one or several maximums or peaks are visible in the wave form of the pulse. As discussed above, using DC energy for ablation procedures involves using high energy levels, increasing the chance of sparking compared to conventional ablation techniques.

The generator preferably comprises a display for displaying the shape of the pulse measured by the measuring unit. The physician is then allowed to inspect the shape of the pulse to ensure no sparking occurred during the last pulse. Preferably the display is further arranged to display an electrocardiogram (ECG) as measured by a connectable electrocardiogram measuring device.

According to a further preferred embodiment, the generator comprises a triggering unit for determining a trigger signal for the discharge of the pulse on the basis of a measured heart rhythm measured by connectable measuring means, wherein the charging unit is arranged to discharge the pulse in accordance with the determined trigger signal. Preferably the generator comprises a suitable connector for connecting heart rhythm measuring means, for instance ECG-measuring means in the form of skin electrodes. This allows for instance an ECG to be used allowing triggered discharge of the pulse in synchronisation with the hearth rhythm, i.e. the QRS-complex. Triggering as such is known in the art.

The triggering unit, which may be formed integrally with the control unit, then determines the exact triggered moment for discharge and the charging unit, for instance under control of the control unit, discharges the pulse on the exact moment in the heart rhythm, for instance at the earliest possible moment after the physician actuated the fire button. The generator is preferably arranged to display the ECG with the triggering signal on the display, allowing the physician to ensure that triggering is performed correctly.

The control unit is preferably arranged to detect an abnormality in the measured pulse shape. The generator may output the detected abnormality, for instance using an output device, for instance in the form of an audio output device or a display. Preferably the control unit is arranged to suppress or adjust the pulse discharge in case an abnormality is detected. The control unit may for instance be arranged to compare the measured shape of the pulse with a preset shape and notify the physician in case a predetermined difference between the shapes is detected. The control unit is preferably arranged to alter the discharge of the pulse, preferably by suppressing discharges, in case an abnormality is detected. It may also be possible that the control unit comprises analysing means for deriving parameters from the measured shape and determine on the basis of these parameters whether a normal or abnormal pulse is discharged.

It is custom to use an Electro Physiological (EP) recording system during ablation procedures. Such a system records and displays measured electrograms (EG's) and signals obtained by various measuring catheters. Such a system typically comprises an EP amplifier for amplifying the measured signals and an EP recorder for recording the signals. According to a further preferred embodiment the catheter lead is further connectable to an EP recorder via a switching device, wherein the switching device is arranged to disconnect the EP EP recorder during discharge of a pulse. Also the catheter used for the ablation can be used for measuring using the EP recorder. The generator is thus preferably provided with a connector for connecting the catheter lead to the EP recording device. To protect the EP recording device, in particular the amplifier thereof, the switching device disconnects the catheter lead connectable to the EP recorder during the discharge of a pulse. The EP signals may be coupled to the triggering unit for determining a trigger for the discharge.

A further preferred embodiment of the generator comprises a plurality of catheter leads for connecting a catheter comprising a plurality of electrodes, wherein the measuring unit is arranged between the indifferent lead and the plurality of catheter leads. Using a catheter provided with a plurality of electrodes in an ablation procedure allows creating lesions at each electrode, preferably adjacently located lesions for creating a non-conductive pathway in the heart tissue. The charging unit is hereby arranged to supply a pulse between each of catheter electrodes and the indifferent electrode. It should be noted that the generator for connecting a multi-electrode may even be used without a measuring unit.

According to a further preferred embodiment, the charging unit is arranged to discharge at least two pulses with different voltages to at least two catheter leads. Connectable to these leads are two different electrodes of the catheter. The charging unit may therefore comprise at least two different charging units, for instance capacitors. A difference in voltage between electrodes on the tissue improves the formation of a closed path of ablated tissue due to current flowing from a higher to a lower potential on the tissue. Preferably the generator, more specifically the charging unit and a connector for connecting a multi-electrode catheter is arranged such that a difference in voltage is applied to adjacent electrodes on the catheter.

The measuring unit can be arranged to measure the total electrical properties of the catheter leads, it is however preferred if the measuring unit is arranged to measure electrical properties of each of the catheter leads individually. This for instance allows the physician to detect sparking at each individual electrode and/or detect individual electrode malfunction.

The invention further relates to a combination of a generator according to the invention and a catheter, preferably a catheter comprising a plurality of electrodes. The invention furthermore relates to a catheter provided with a plurality of electrodes for use in DC ablation procedures.

The invention furthermore relates to a method for providing an electrical pulse between two electrode leads, comprising the steps of:
  determining a magnitude of the pulse;
  charging an amount of electrical energy;
  measuring an electrical property between the leads, preferably at least one of the impedance and the difference in voltage between the leads, and;
  discharging the amount of electrical energy in the pulse of predetermined magnitude between the leads.

The step of measuring the impedance is preferably executed prior to charging the amount of energy to allow charging an amount of electrical energy that depends on said measured electrical property. The amount of electrical energy to be charged is preferably dependent on the measured impedance between the leads. This allows an accurate determination of the amount of electrical energy to be discharged as already described above.

The measurement of the difference in voltage is preferably executed synchronously with the step of discharging, allowing detection of any abnormalities in the shape of the pulse as discussed above.

According to a preferred embodiment, the method further includes connecting a catheter and an indifferent electrode to the leads. The catheter and the indifferent electrode are operable coupled to a patient. Preferably, the method comprises discharging the pulse between the electrodes of the catheter and the indifferent electrode.

In FIG. 1, a system for use in a direct current ablation procedure is shown. As indicated with the dashed line, the system can be divided in two parts, one part for in the catheterisation lab 100 with a patient 99 and one part for in a control room 200. The generator 1 with housing 1a according to the invention and an EP amplifier 5 are located in the catheterisation lab 100 with the patient 99 and a remote control unit 7 and an EP recorder 6 are located in the control room 200. The EP amplifier connects three measuring catheters 5a-c for measuring EP-signals as is known in the art. The connection between the generator 1 and remote control unit 7 and the connection between the EP amplifier 5 and the EP recorder 6 are optical connectors.

The patient 99 is this example suffers from atrial arrhythmias and is undergoing a DC-ablation procedure for isolating the pulmonary vein antrum. A catheter is introduced in the groin and advanced to the hearth. The catheter 2 is provided with ten electrodes on its distal end, allowing the forming of a closed path of ablated tissue, thereby isolating the tissue.

Figure 2:
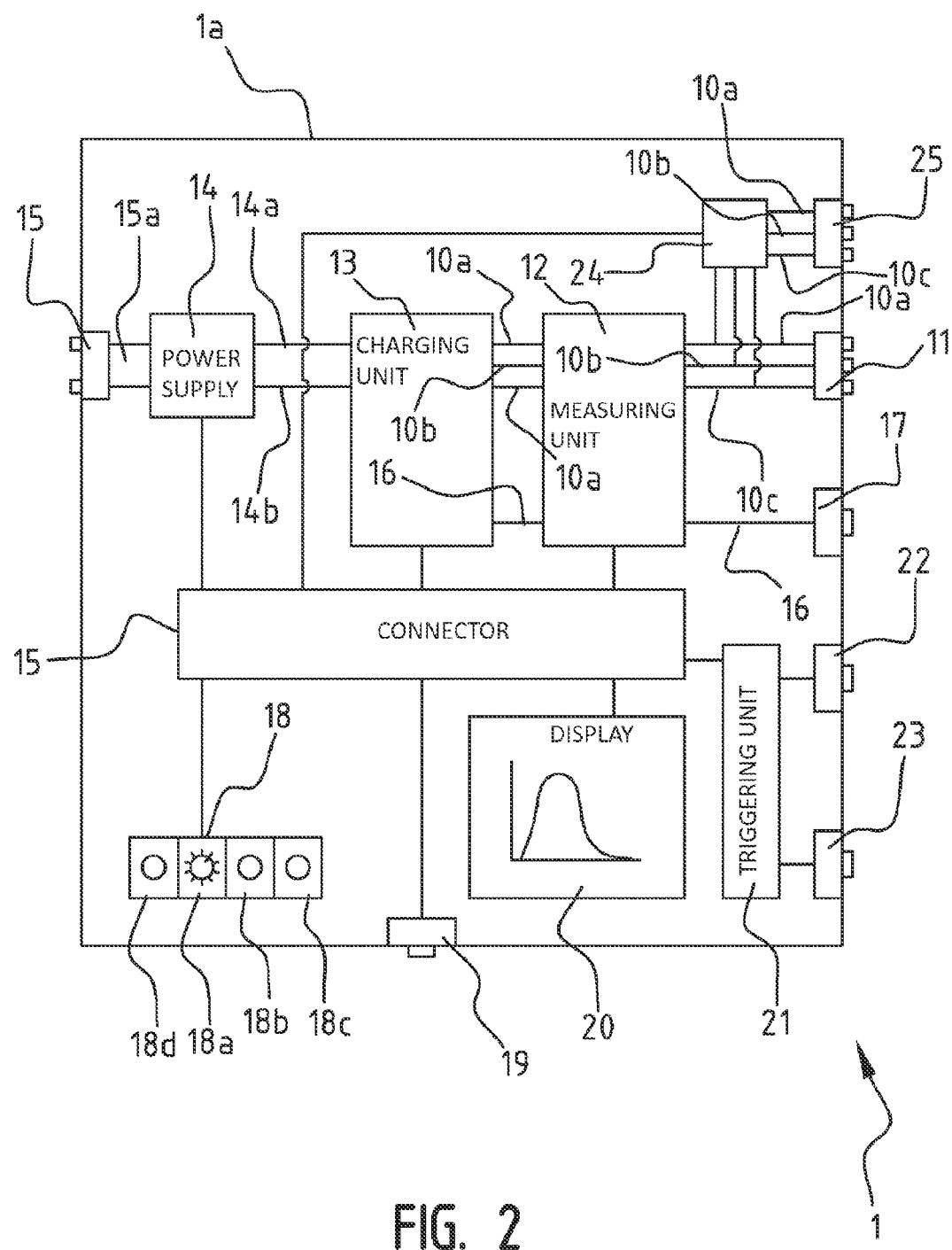
FIG. 2 schematically shows an example of an embodiment of a generator according to the present invention.

The catheter 2 is connected to the generator 1 using a connector 11. The connector 11 is arranged to connect each of the leads leading to each of the electrodes to the generator 1. In FIG. 2, only three different electrode leads 10a-c connected to the connector 11 are shown.

For isolating the tissue, a shock is delivered between the electrodes of the catheter 2 and an indifferent electrode 3 in the form of a skin patch. The indifferent electrode is connected to the generator 1 using a connector 17.

For delivering the shock between the indifferent electrode 3 and the catheter 2, a charging unit 13 is provided in the generator 1, see FIG. 2. The charging unit 13 is capacitive-discharge unit and is provided with a capacitor for charging electrical energy. A power supply 14 provides electrical energy to the charging unit 13. The connections 14a and 14b may for instance be formed as a variable transformer. The power supply 14 is connected by leads 15a to a suitable connector 15. The charging unit 13 is arranged to deliver the shock between the leads 10a-c connecting the catheter 2 via connector 11 and the indifferent lead 16 connecting the indifferent electrode via connector 17.

The power supply 14 and the charging unit 13 are coupled to a control unit 15, provided with a central processing unit, and is arranged to control the charging voltage over the capacitor in the charging unit 13 by adjusting the variable transformer. The amount of electrical energy charged in the charging unit 13 can thus be adjusted.

Connected to the control unit 15 is further the input unit 18. Input unit 18 is provided with a shock amplitude dial 18a, an ECG-trigger level dial 18d, a charging button 18b and a fire button 18c. As shown, the control unit 15 is further connected to a connector 19 for connecting the remote control unit 7. The remote control unit 7 is provided with the same buttons 18a-d, allowing the generator to be operated from the control room 200. Also connected to the generator using a suitable connector 19a 1 is a foot pedal 8. The foot pedal 8 allows a physician to operate the generator 1. More specifically the foot pedal 8 allows firing the generator 1.

With the dial 18a, the physician can input the magnitude of the shock to be delivered to the patient 99. According to the invention, the physician can input the magnitude in terms of Joules to be delivered to the tissue between the electrodes 2 and 3, as will be explained in more detail below. In for instance defibrillators, it is custom to input the charging voltage of the charging unit 13. A range of 100 to 400 Joules can be inputted with the dial 18a.

On actuation of the charge-button 18b, the power supply 14 and the charging unit 13 are instructed to charge an amount of electrical energy. This amount of electrical energy is determined on the basis of measurements from a measuring unit 12.

According to the invention, the generator 1 is provided with a measuring unit 12 to measure electrical properties of the leads 10a-c and 16. In particular, the measuring unit 12 is arranged to determine the impedance or resistance between the catheter electrodes 10a-c and the indifferent lead 16 when no shock for ablating tissue is being delivered between the indifferent electrode 3 and the catheter 2. The measured impedance is then a measure of the impedance of the tissue of the patient 99, as the indifferent electrode 3 and the catheter 2 are already in place.

Since the impedance between the electrodes 10a-c and 16 are known, the charging voltage can be adjusted to provide a pulse with a known electrical charge to the patient 99. As DC ablation uses relatively high amounts of energy, this adjustment of the amount of energy provided to the patient ensures that the amount of delivered energy is correct.

Also provided on the input unit 18 is an ECG trigger level dial 18d. This dial 18d allows the physician to input the threshold level to adjust triggering level manually. As can be seen in FIG. 1, patches 4 for measuring the ECG are connected to the patient 99. The patches 4 are connected using a connector 22 to the generator. The generator 1 is further provided with a triggering unit 21 which determines a triggering signal from the supplied ECG data. This allows triggered delivery of the shock. In this case, the dial 18d is not needed. The triggering signal is outputted to connector 23 to allow the supply of the triggering signal to the EP amplifier 5. The triggering signal is further provided to the control unit 15 and the control unit 15 is arranged to discharge the charging unit 13 in synchronization with the triggering signal on actuation of the fire button 18c.

Figure 3:
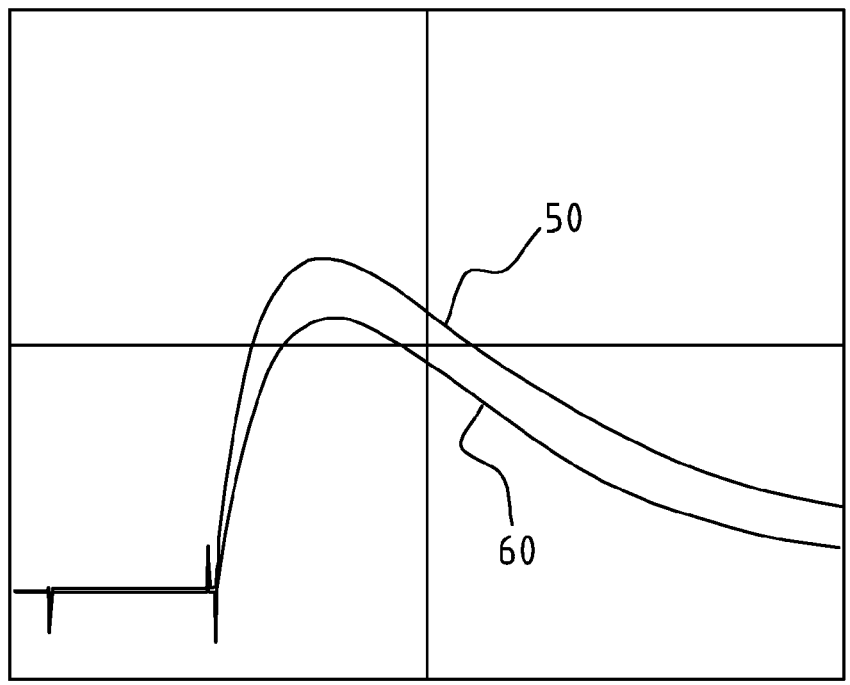
FIGS. 3 and 4 schematically show examples of two measured pulse shapes according to embodiments of the present invention.

The charging unit 13 hereby discharges the electrical energy over an inductor and the charging unit is arranged to discharge a mono-phasic electrical pulse. The pulse hereby has a shape as seen in FIG. 3, wherein the line 50 indicates the difference in voltage between the electrodes and the line 60 indicates the current.

In order to measure the shape of the discharged pulse, the measuring unit 12 is arranged to measure the current and the difference in voltage over time. The shape of the pulse can be displayed on display 20. Display 20 can further show the ECG-data with triggering signal.

Figure 4:
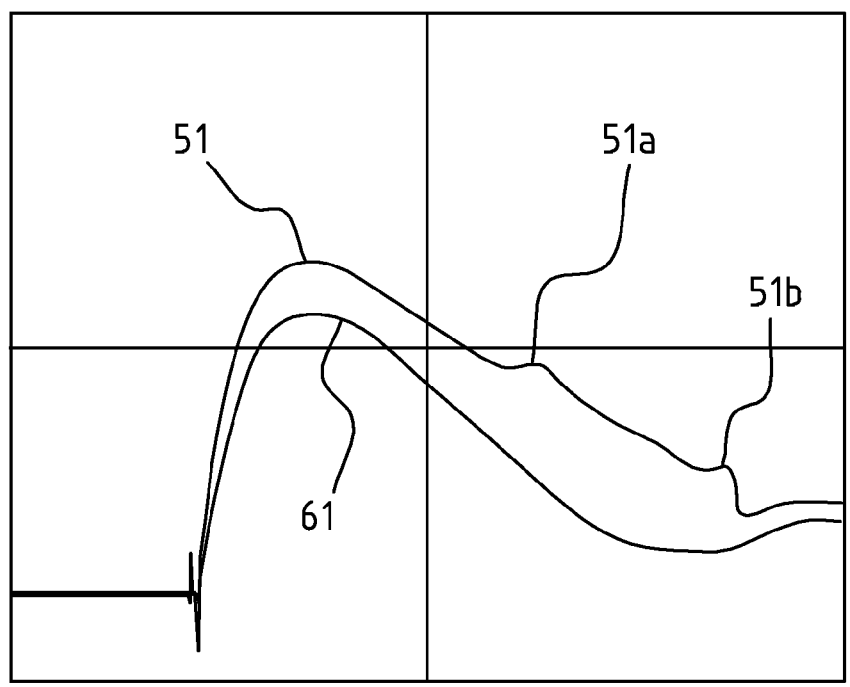

The control unit 15 is further arranged to detect abnormalities in the shape of the pulse. In this example, irregularities in the voltage difference are monitored. A typical irregularity is shown in FIG. 4, wherein the voltage difference curve 51 shows two peaks 51a and 51b. The peaks 51a and 51b are indicators that sparking occurs at at least one of the electrodes of the catheter. The control unit 15 is arranged to detect these irregularities and to provide output in case an abnormality is detected. Discharge by the charging unit 12 is further suppressed.

The generator is further provided with a connector 25 connecting the electrode leads 10a-c to the EP amplifier 5. The catheter 2 can then be used for recording EP signals. However, to protect the EP amplifier 5, the leads 10a-c are coupled to the connector via switch 24. The switch 24 is arranged to decouple the leads 10a-c from the connector in case a shock is delivered. The switch 24 is hereto operable coupled to the control unit 15.

In this example, the measuring unit 12 measures the impedance and difference in voltage between the combination of leads 10a-c and the indifferent lead 16. However, to indentify sparking at a single electrode, it may be possible to measure the difference in voltage over time between each of leads 10a-c and the indifferent lead 16. The same applies for the impedance.

The present invention is not limited to the embodiment shown, but extends also to other embodiments falling within the scope of the appended claims.

The invention claimed is:

1. A generator for use in an ablation procedure, comprising:
   an indifferent lead and a catheter lead for connecting an indifferent electrode and a catheter provided with at least one electrode;
   a charging unit arranged to charge an amount of electrical energy and to discharge an electrical pulse of a predetermined magnitude between the indifferent lead and the catheter lead; a power supply arranged to supply electrical energy to the charging unit, wherein the electrical pulse comprises a DC ablation pulse, and wherein the DC ablation pulse is discharged in less than 10 ms;
   an input unit arranged for inputting an indication of the magnitude of the electrical pulse;
   a measuring unit arranged between the indifferent lead and the catheter lead for measuring at least one electrical property between the indifferent lead and the catheter lead, wherein the measuring unit is arranged to measure an impedance of a patient between the indifferent lead and the catheter lead when the indifferent lead and the catheter lead are in place on the patient, when no electrical pulse for ablating tissue is being discharged between the indifferent lead and the catheter lead in place on the patient, and prior to discharge of the electrical pulse for ablating tissue; and
   a control unit arranged to adjust the magnitude of the electrical pulse discharged by the charging unit based on the impedance measured by the measuring unit.

2. The generator of claim 1, wherein the input unit is arranged to input an electrical charge setting as a measure of the indication of the magnitude of the electrical pulse and wherein the control unit is arranged to adjust the amount of charged energy in the charging unit on the basis of the measured impedance for discharging the electrical pulse between the indifferent lead and the catheter lead with the inputted electrical charge setting.

3. The generator of claim 1, wherein the input unit is arranged to input an electrical current setting as a measure of the indication of the magnitude of the electrical pulse and wherein the control unit is arranged to adjust the amount of charged energy in the charging unit on the basis of the measured impedance for discharging the electrical pulse between the indifferent lead and the catheter lead with the inputted electrical current setting.

4. The generator of claim 1, wherein the measuring unit is further arranged to measure an electrical property of the electrical pulse over a time period of the electrical pulse.

5. The generator of claim 4, further comprising a display for displaying a shape of the electrical pulse measured by the measuring unit, wherein the display is further arranged to display an electrocardiogram (ECG) as measured by a connectable ECG measuring device.

6. The generator of claim 5, wherein the control unit is arranged to detect an abnormality in the shape of the measured electrical pulse and wherein the generator is arranged to provide output in case an abnormality is detected.

7. The generator of claim 4, wherein the measured electrical property of the electrical pulse is a voltage difference between the indifferent lead and the catheter lead over the time period of the electrical pulse.

8. The generator of claim 1, wherein at least one of the indifferent lead and the catheter lead is further connectable to an electrophysiology (EP) recorder via a switching device, wherein the switching device is arranged to disconnect the EP recorder during discharge of the electrical pulse.

9. The generator of claim 1, further comprising a triggering unit for determining a trigger signal for the discharge of the electrical pulse on the basis of a measured heart rhythm measured by connectable measuring means, wherein the charging unit is arranged to discharge the electrical pulse in accordance with the determined trigger signal.

10. The generator of claim 1, wherein the catheter lead comprises one of a plurality of catheter leads of the generator for connecting a catheter comprising a plurality of electrodes, wherein the measuring unit is arranged between the indifferent lead and the plurality of catheter leads.

11. The generator of claim 10, wherein the measuring unit is arranged to measure electrical properties of each of the catheter leads individually.

12. The generator of claim 1, wherein the charging unit is arranged to discharge the electrical pulse with a magnitude between approximately 100 to 400 Joules.

13. The generator of claim 1, wherein the measuring unit is arranged to determine the impedance when the indifferent lead is on an exterior of the patient.

14. The generator of claim 1, wherein the electrical pulse is discharged over 60 Ohms.

15. The generator of claim 1, wherein the electrical pulse is discharged with a length between 2 ms and 10 ms.

16. A method for providing an electrical pulse to tissue of a patient between two electrode leads, comprising:
 (a) determining a magnitude of the electrical pulse;
 (b) charging an amount of electrical energy;
 (c) measuring an impedance of the tissue between the leads when no electrical pulse for ablating tissue is being discharged to the tissue;
 (d) following step (c), discharging the amount of electrical energy in the electrical pulse of magnitude determined in step (a) to the tissue between the leads wherein the electrical pulse comprises a DC ablation pulse, wherein the DC ablation pulse is discharged in less than 10 ms, and wherein the amount of electrical energy that is discharged is based on the measured impedance in step (c); and
 (e) adjusting, using a control unit, the magnitude of the electrical pulse discharged by a charging unit based on the impedance measured by a measuring unit.

17. The method of claim 16, further comprising: inputting, using an input unit, an electrical charge indication as a measure of the magnitude of the electrical pulse; and adjusting, using the input unit, the amount of charged energy in the charging unit based on the measured impedance for discharging the electrical pulse between the leads with the inputted electrical charge indication.

18. The method of claim 16, further comprising: displaying, using a display unit, a shape of the electrical pulse measured by the measuring unit, and an electrocardiogram as measured by a connectable ECG measuring device.

* * * * *